(12) United States Patent
Yuan et al.

(10) Patent No.: US 9,173,852 B2
(45) Date of Patent: Nov. 3, 2015

(54) GLYCYRRHETINIC ACID-MEDIATED NANOPARTICLES OF HEPATIC TARGETED DRUG DELIVERY SYSTEM, PROCESS FOR PREPARING THE SAME AND USE THEREOF

(75) Inventors: Zhi Yuan, Tianjin (CN); Wei Huang, Tianjin (CN); Qin Tian, Tianjin (CN); Chuangnian Zhang, Tianjin (CN); Liang Han, Tianjin (CN); Tong Liu, Tianjin (CN); Yue Zhang, Tianjin (CN); Yue Chen, Tianjin (CN)

(73) Assignees: TIAN SI POLYMER MATERIALS TECHNOLOGY DEVELOPMENT CO., Tianjin (CN); NANKAI UNIVERSITY, Tianjin (CN)

( * ) Notice: Subject to any disclaimer, the term of this patent is extended or adjusted under 35 U.S.C. 154(b) by 927 days.

(21) Appl. No.: 12/338,966

(22) Filed: Dec. 18, 2008

(65) Prior Publication Data

US 2009/0252803 A1     Oct. 8, 2009

(30) Foreign Application Priority Data

Apr. 8, 2008   (CN) .......................... 2008 1 0052635
Apr. 8, 2008   (CN) .......................... 2008 1 0052636

(51) Int. Cl.
*A61K 9/51*       (2006.01)
*A61K 47/36*      (2006.01)
*A61K 47/48*      (2006.01)

(52) U.S. Cl.
CPC ............ *A61K 9/5146* (2013.01); *A61K 9/5161* (2013.01); *A61K 9/5192* (2013.01); *A61K 47/482* (2013.01); *A61K 47/4823* (2013.01); *A61K 47/48215* (2013.01); *A61K 47/48315* (2013.01); *A61K 47/48907* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 5,543,158 A * | 8/1996 | Gref et al. ..................... | 424/501 |
| 7,348,030 B1 | 3/2008 | Sung et al. | |
| 2001/0051189 A1 * | 12/2001 | Fernandez et al. ............ | 424/499 |
| 2004/0166158 A1 * | 8/2004 | Davis et al. .................... | 424/468 |
| 2006/0073209 A1 * | 4/2006 | Sung et al. .................... | 424/501 |
| 2006/0134785 A1 * | 6/2006 | Fernandez et al. ............ | 435/375 |

FOREIGN PATENT DOCUMENTS

| | | | |
|---|---|---|---|
| CN | 1586488 A | | 3/2005 |
| CN | 1743008 A | | 3/2006 |
| CN | 1743008 A | * | 3/2006 |
| CN | 101006983 A | | 8/2007 |
| CN | 101006983 A | * | 8/2007 |

OTHER PUBLICATIONS

Y Wu, W Yang, C Wang, J Hu, S Fu. "Chitosan Nanoparticles as a Novel Delivery System for Ammonium Glycyrrhizinate." International Journal of Pharmaceutics, vol. 295, 2005, pp. 235-245.*

(Continued)

*Primary Examiner* — Isaac Shomer
(74) *Attorney, Agent, or Firm* — James B. Conte; Husch Blackwell LLP

(57) ABSTRACT

Disclosed are a hepatic targeted drug delivery system and a process for preparing the same. Also disclosed is a method for treating liver cancer.

18 Claims, 13 Drawing Sheets

(a)

(b)

(56) References Cited

OTHER PUBLICATIONS

Derwent English Abstract for CN 101006983 A. Aug. 1, 2007. 2 pages.*
CAS Registry Record for 471-53-4 (Glycyrrhetic acid). Entered STN Nov. 16, 1984. 2 printed pages.*
CAS Registry Record for 1405-86-3 (Glycyrrhizin). Entered STN Nov. 16, 1984. 2 printed pages.*
Yuan Zhi Zha. "Method for Preparing Nano Liver-Target Biodegradating Medicine Carrier Material." English Translation of CN 1743008 A. Machine Translation obtained on Mar. 24, 2014. Original Patent published on Mar. 8, 2006. 22 printed pages.*
S Cammas, K Kataoka. "Functional poly[(ethylene oxide)-co-(b-benzyl-L-aspartate)] Polymeric Micelles: Block Copolymer Synthesis and Micelles Formation." Macromolecular Chemical Physics, vol. 196, 1995, pp. 1899-1905.*
CS Cho, JW Nah, YI Jeong, JB Cheon, S Asayama, H Ise, T Akaike. "Conformational transition of nanoparticles composed of poly(g-benzyl l-glutamate) as the core and poly(ethylene oxide) as the shell." Polymer, vol. 40, 1999, pp. 6769-6775.*
Sheng-Jun Mao et al., "Uptake of Albumin Nanoparticle Surface Modified with Glycyrrhizin by Primary Cultured Rat Hepatocytes", 2005 (pp. 3075-3079).
Sayoko Osaka et al., "Uptake of Liposomes Surface-Modified with Glycyrrhizin by Primary Cultured Rat Hepatocytes" 1994 (pp. 940-943).
Stockert et al., "Hepatic Binding Protein: The Galactose-Specific Receptor of Mammalian Hepatocytes", 1983 (pp. 750-757).
Aaron Ciechanover et al., "Sorting and Recycling of Cell Surface Receptors and Endocytosed Ligands: The Asialoglycoprotein and Transferrin Receptors", 1983 (pp. 113-136).
Negishi et al., "Specific Binding of Glycyrrhetinic Acid to the Rat Liver Membrane", 1991 (pp. 77-82).
Lin et al., "Glycyrrhizin Surface-Modified Chitosan Nanoparticles for Hepatocyte-Targeted Delivery", dated 2008 (7 pages).
Mao et al., "Uptake of Albumin Nanoparticle Surface Modified with Glycyrrhizin by Primary Cultured Rat Hepatocytes", May 28, 2005 (5 pages).
Tsuji et al., "Targeting of Liposomes Surface-Modified with Glycyrrhizin to the Liver. 1. Preparation and Biological Disposition", 1991 (5 pages).
English Translation of the Title, Abstract, Claim and Examples 1-5 of Lin et al. CN101006983 A, published Aug. 1, 2007.

* cited by examiner (a)

(b)

GLYCYRRHETINIC ACID-MEDIATED NANOPARTICLES OF HEPATIC TARGETED DRUG DELIVERY SYSTEM, PROCESS FOR PREPARING THE SAME AND USE THEREOF

CROSS REFERENCE TO RELATED APPLICATIONS

The present application claims to the benefits of Chinese patent application Nos. 200810052635.0, filed on Apr. 8, 2008 entitled "nanoparticles based on amphiphilic block copolymers as hepatic targeted deliver system and process for preparing the same" and 200810052636.5, filed on Apr. 8, 2008 entitled "nanoparticles based on glycyrrhetinic acid-polyethylene glycol/chitosan as hepatic targeted deliver system and process for preparing the same", which are explicitly incorporated herein by reference in their entireties.

BACKGROUND OF THE INVENTION

1. Field of the Invention

The present application relates to a hepatic targeted drug delivery system, a process for preparing the same and a method for treating liver cancer.

2. Description of the Related Art

Primary liver cancer is one of the most leading causes of death in China, which is only exceeded by gastric cancer and accounts for 45% of the total death caused by liver cancer all around the world. In addition, the five-year survival rate is merely 5%.

At present, treatment for liver cancer mainly depends on organ transplantation, radiotherapy, chemotherapy and the like. However, liver transplantation is limited by the shortage of donors and the potential immunologic rejection, while the radiotherapy always causes directly damage to bile duct. Therefore, the chemotherapy has become the mainstream for liver cancer treatment. However, the conventional chemotherapy is ineffective, mostly due to the disadvantages of short half-life time in blood stream, high overall clearance rate and poor selectivity for the desired site. In addition, liver has the ability to resist drugs. Low dosage of drugs is ineffective for liver cancer treatment while high dosage may cause toxicity for other organs. Therefore, the development of controlled release and hepatic targeted drug delivery system is primarily important.

Recently, hepatic targeted drug delivery system has attracted much attention because it provides a high degree of selectivity to liver, enhances the uptake ability of drug-loaded nanoparticles into target sites, reduces drug doses and significantly decreases drug toxicity.

However, the development of hepatic targeted drug delivery system is a bit slow. Some researchers have attempted to increase the tissue specificity of drug carriers by coupling with targeting agents, such as monoclonal antibodies. However, antibodies are costly and difficult to be obtained. In addition, as most of them come from mice, the bio-security becomes the major concerns.

In recent years, the receptor-mediated hepatic targeted drug delivery system has attracted more attention because it is a promising way to transfer drug to the desired sites. Once a ligand is bound to a receptor, a ligand-receptor complex is rapidly internalized and the receptor recycles back to the surface (Ciechanover, A., Schwartz, A L. Lodish, H. F. Sorting and recycling of cell surface receptors and endocytosed ligands: the asialoglycoprotein and transferrin receptors. *J. Cell. Biochem.*, 1983, 23(1-4), 107-130). Asialoglycoprotein receptor (ASGPR) is known as to be present on hepatocytes and several human hepatoma cell lines which shows a strongly affinity with galactose residues. Extensive studies have focused on the ASGPR-mediated hepatic targeted drug delivery system. For example, Hsing-Wen Sung, et al. in U.S. Pat. No. 7,348,030 B 1 discloses nanoparticles for targeting hepatoma cells. In particular, nanoparticles comprised by poly(γ-glutamic acid)-block-polylactide and conjugated with galactosamine are disclosed. The in vitro experimental results show that these nanoparticles have high affinity to hepatoma cells. However, it has been reported that there are inhibitors in serum of a subject in pathologic status, which lead to low recognition of ASGPR for galactose residues (Stockert R. J., Morell A. G. Hepatic binding protein: the galactose-specific receptor of mammalian hepatocytes, *Hepatology*, 1983, 3: 750-757). Therefore, the development of a new hepatic targeted ligand instead of the conventional one is very necessary.

Liquorice mainly distributes in the west of China and has been widely used in the prescription of traditional Chinese medicine. Glycyrrhizin and glycyrrhetinic acid can be isolated from its root easily. In 1991, Negishi confirmed that the rat liver cell membrane contains a large number of binding sites for glycyrrhetinic acid and a small number of binding sites for glycyrrhizin (Negishi M., Irie A., Nagata N., et al. Specific binding of glycyrrhetinic acid to the rat liver membrane, *Biochim. Biophys. Acta.*, 1991, 1066: 77-82). Since then, studies on the hepatic targeted drug delivery system mediated by glycyrrhizin and glycyrrhetinic acid has drawn the focus of most researchers. Subsequently, some Chinese and foreign researchers reported that when liposome or serum albumin was modified with glycyrrhizin/glycyrrhetinic acid, it exhibits a considerably high affinity to liver than that of the unmodified ones (Sayoko Osaka, Hideki Tsuji, Hiroshi Kiwada. Uptake of liposomes surface-modified with glycyrrhizin by primary cultures rat hepatocytes, *Biol. Pham. Bull.*, 1994, 17: 940-943; Sheng-jun Mao, Shi-xiang Hou, Ru He, et al. Uptake of albumin nanoparticle surface modified with glycyrrhizin by primary cultured rat hepatocytes. *World J. Gastroentenol.*, 2005, 11: 3075-3079). However, liposome is limited as a drug delivery carrier due to several factors such as the rapid uptake by the reticuloendothelial system (RES), quick clearance from blood stream and the leakage of their loading content before reaching the targeting sites. Therefore, some new drug carriers should be taken into consideration.

During the last decade, biomedical polymers, especially the biodegradable and biocompatible polymers develop rapidly, promoting the development of drug controlled release field. Moreover, with the cross-integration of materials science, biomedicine and molecular biology, the developing process has also been accelerated. Polymeric nanoparticles can protect drugs from being uptaken by the RES, thereby enhancing drug stability, increasing the efficacy and prolonging the circulation time in blood, and the loaded drug can be targeted to the desired sites with a sustained release profile. Currently, much attention has been paid to the nanoparticles made from natural polysaccharide such as chitosan or its derivatives and sodium alginate. Moreover, synthetic poly(amino acid)-ester and polyester are also gained considerable attention.

The hepatic targeted drug delivery system mediated by glycyrrhizin or glycyrrhetinic acid (components of traditional Chinese drug) is seldom reported in the world except in China. For example, Yingli ZHENG, et al. in Chinese patent application No. 200410052767.5 discloses glycyrrhizin-modified chitosan nanoparticles and process for preparing the same. Yiming LIU, et al. in Chinese patent application No.

200710062813.3 discloses a process for preparing glycyrrhetate-modified chitosan/carboxyl-chitosan complex nanoparticles.

Up to now, the glycyrrhetinic acid-mediated hepatic targeted drug delivery system has solely been reported by Zhi YUAN, et al. in Chinese patent application No. 200510015172.7.

BRIEF SUMMARY OF THE INVENTION

In one aspect of the present application, there is provided a nanoparticle of a hepatic targeted drug delivery system comprising a carrier and an anticancer agent, wherein the carrier is modified with glycyrrhetinic acid.

In another aspect of the present application, there is provided a process for preparing a nanoparticle of a hepatic targeted drug delivery system comprising
(a) modifying a carrier with glycyrrhetinic acid; and
(b) loading an anticancer agent to the carrier modified with glycyrrhetinic acid In another further aspect of the present application, there is provided a pharmaceutical composition comprising a nanoparticle of a hepatic targeted drug delivery system and a pharmaceutically acceptable excipient, wherein the nanoparticle comprises a carrier and an anticancer agent and the carrier is modified with glycyrrhetinic acid.

In another further aspect of the present application, there is provided a method for treating liver cancer in a mammal comprising administering a therapeutically effective amount of nanoparticles of a hepatic targeted drug delivery system, wherein the nanoparticle comprises a carrier and an anticancer agent and the carrier is modified with glycyrrhetinic acid.

DETAILED DESCRIPTION OF THE INVENTION

Figure 1:
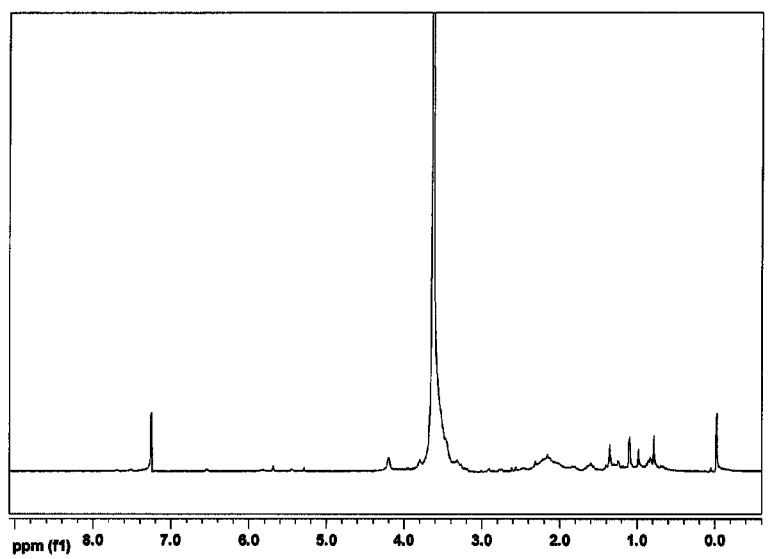
FIG. 1 illustrates the $^1$H NMR spectrum of GA-PEG$_{3400}$ prepared in Example 5.

In the following description, certain specific details are included to provide a thorough understanding of various disclosed embodiments. One skilled in the relevant art, however, will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, which is as "including, but not limited to".

Reference throughout this specification to "one embodiment", or "an embodiment", or "in another embodiment", or "some embodiments", or "in some embodiments" means that a particular referent feature, structure, or characteristic described in connection with the embodiment is included in at least one embodiment. Thus, the appearance of the phrases "in one embodiment", or "in an embodiment", or "in another embodiment", or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a", "an", and "the" include plural referents unless the content clearly dictates otherwise. In this application, the use of "or" means "and/or" unless stated otherwise.

In one aspect of the present application, there is provided a nanoparticle of a hepatic targeted drug delivery system comprising a carrier and an anticancer agent, wherein the carrier is modified with glycyrrhetinic acid.

In some embodiments of the present application, the particle size of the nanoparticle is in the range of about 50 to 450 nm.

In some embodiments of the present application, the loading content of an anticancer agent is in the range of about 2 to 20% by weight of the nanoparticles.

In some embodiments of the present application, the weight of the glycyrrhetinic acid is in the range of about 1-30% by weight of the carrier.

In some embodiments of the present application, the carrier is made of a biodegradable polymer.

Exemplary biodegradable polymer that can be used in the present application includes, but is not limited to, a complex of polyethylene glycol (PEG) and naturally occurring polysaccharide, polyethylene glycol-poly(amino acid) ester and diamine-polyester.

In some preferred embodiments of the present application, a nanoparticle of a hepatic targeted drug delivery system comprising a carrier and an anticancer agent, wherein the carrier is a complex of polyethylene glycol (PEG) and naturally occurring polysaccharide or derivatives thereof and is modified with glycyrrhetinic acid.

In some preferred embodiments of the present application, a nanoparticle of a hepatic targeted drug delivery system comprising a carrier and an anticancer agent, wherein the carrier is a polyethylene glycol-poly(amino acid) ester and is modified with glycyrrhetinic acid.

In some preferred embodiments of the present application, a nanoparticle of a hepatic targeted drug delivery system comprising a carrier and an anticancer agent, wherein the carrier is a diamine-polyester and is modified with glycyrrhetinic acid.

In some embodiments of the present application, the polyethylene glycol (PEG) is a diamine-terminal derivative of polyethylene glycol.

In some preferred embodiments of the present application, the diamine-terminal derivative of polyethylene glycol has a molecular weight of about 2,000 to 20,000 Da.

Chitin is an unbranched linear polysaccharide of N-acetyl-D-glucosamine units linked by β-1,4 bonds. The exoskeletons of insects and crustacea, e.g., crabs, lobsters and shrimps, contain large amounts of chitin, making this polysaccharide nature's second most plentiful biopolymer next to cellulose. However, chitin is not readily processible or usable since it is inert to many common aqueous and organic solvents. Attempts have been made to provide processible derivatives of chitin, and processible derivatives of chitin such as chitosan and derivatives thereof are known in the art. Chitosan is partially or completely deacetylated chitin and is a polysaccharide consisting basically of monomeric β(1-4)-D-glucosamine (A) units and monomeric β(1-4)-N-acetyl-D-glucosamine (B) units which are scattered randomly in the molecule of the polymer, wherein the polysaccharide contains at least about 60% of A and up to about 40% of B. Chitosan can be derivatized, e.g., carboxymethylated, to provide additional and/or different functional properties. Chitosan and derivatives thereof are typically soluble in acids, including mild acids, e.g., formic, acetic and propionic acids, and depending on the types of modification, certain chitosan derivatives, e.g., O-carboxymethyl chitosan, are soluble even in water.

Suitable chitosan and derivatives thereof that can be used for the present application include water-insoluble and water-soluble chitosan and chitosan derivatives, and water-soluble chitin derivatives. Water-insoluble chitosan suitable for the present application includes, but is not limited to, non-derivatized chitosan and chitosan derivatives that, for example, contain an alkyl group which does not have a dissociable functional moiety. Exemplary water-insoluble chitosan derivatives include, but are not limited to N-alkyl chitosan, 6-alkyloxy chitosan, N,O-alkyl chitosan, N,N-dialkyl chitosan and N-halochitosan. Of the water-insoluble chitosan and chitosan derivatives, chitosan is particularly suitable. Water-soluble chitosan derivatives suitable for the present application include, but are not limited to, chitosan polymers having one or more hydrophilic substituents at 2-N and/or 6-position of the glucosamine. Exemplary hydrophilic substituents for water-soluble chitosan derivatives include, but are not limited to, carboxyalkyl, e.g., carboxymethyl, carboxyethyl, carboxypropyl and carboxybutyl; hydroxyalkyl, e.g., hydroxyethyl, hydroxypropyl, hydropybutyl; sulfuryl; phosphoryl; amino and the like. Suitable water-soluble chitosan derivatives include, but are not limited to glycol chitosan, O-carboxymethyl chitosan, O-carboxyethyl chitosan, O-carboxypropyl chitosan, O-carboxybutyl chitosan, N,O-carboxymethyl chitosan, N-carboxymethyl chitosan, N,O-sulfur chitosan, 1-deoxygalactit-1-yl-chitosan, 1-deoxygalucit-1-yl-chitosan and N,O-ethylamine chitosan, hydroxymethyl chitosan, hydroxyethyl chitosan, hydroxypropyl chitosan, hydroxyisopropyl chitosan, hydropybutyl chitosan and N-(2-hydroxyl)-propyl-3-trimethyl ammonium chitosan chloride (HTACC). Water-soluble non-deacetylated chitin derivatives suitable for the present application include, but are not limited to, N,O-ethylamine chitin and O-sulfur chitin.

In some preferred embodiments of the present application, the chitosan derivatives are selected from the group consisting of glycol chitosan, 300-carboxymethyl chitosan, O-carboxyethyl chitosan, O-carboxypropyl chitosan, O-carboxybutyl chitosan, N,O-carboxymethyl chitosan, N-carboxymethyl chitosan, N,O-sulfur chitosan, 1-deoxygalactit-1-yl-chitosan, 1-deoxygalucit-1-yl-chitosan and N,O-ethylamine chitosan, hydroxymethyl chitosan, hydroxyethyl chitosan, hydroxypropyl chitosan, hydroxyisopropyl chitosan, hydropybutyl chitosan and N-(2-hydroxyl)-propyl-3-trimethyl ammonium chitosan chloride (HTACC).

Exemplary naturally occurring polysaccharide that can be used in the present application includes, but is not limited to, a chitosan having a degree of deacetylation of above 70%, a derivative of the chitosan and an alginate.

In some embodiments of the present application, the chitosan and the derivative of chitosan have a molecular weight of about 3,000 to 200,000 Da.

In some embodiments of the present application, the alginate has a molecular weight of about 50,000 to 200,000 Da.

Exemplary alginate that can be used in the present application includes, but is not limited to, sodium alginate, potassium alginate, calcium alginate and ammonium alginate.

Exemplary poly(amino acid)-ester that can be used in the present application includes, but are not limited to, poly(γ-methyl-L-glutamate), poly(γ-benzyl-L-glutamate), poly(γ-methyl-L-aspartate) and poly(γ-benzyl-L-aspartate).

In some embodiments of the present application, the poly(amino acid)-ester has a molecular weight of about 2,000 to 50,000 Da.

The poly(amino acid)-ester used in the present application are easily obtained by the ring open polymerization of each N-carboxyanhydride (NCA) monomer.

In some embodiments of the present application, some of the NCA monomers are listed as follows.

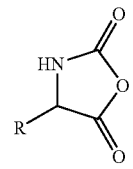

R = CH$_2$CH$_2$COOCH$_3$    γ-methyl-L-glutamate N-carboxyanhydride (MLG-NCA)

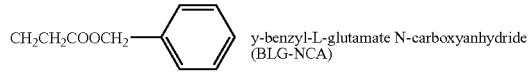

γ-benzyl-L-glutamate N-carboxyanhydride (BLG-NCA)

CH$_2$COOCH$_3$    γ-methyl-L-aspartate N-carboxyanhydride (MLA-NCA)

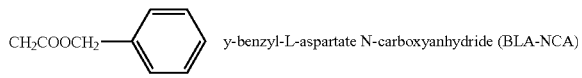

γ-benzyl-L-aspartate N-carboxyanhydride (BLA-NCA)

Exemplary diamine that can be used in the present application includes, but is not limited to, ethylenediamine, 1,2-propanediamine, 1,3-propanediamine, 1,4-butanediamine, 1,3-pentanediamine, 1,5-pentanediamine, 2-methyl-1,5-pentanediamine, hexanediamine, and diaminopolyethylene glycol.

In some preferred embodiments of the present application, the diamine is selected from the group consisting of ethylenediamine, 1,3-propanediamine, hexanediamine and diaminopolyethylene glycol having a molecular weight of about 2,000 to 20,000 Da.

Exemplary polyester that can be used in the present application includes, but is not limited to, polylactide, polycaprolactone, polyglycolide, copolymers of lactide and glycolide, copolymers of caprolactone and glycolide and copolymers of lactide and caprolactone.

In some embodiments of the present application, the polyester has a molecular weight of about 2,000 to 50,000 Da.

Exemplary anticancer agent that can be used in the present application includes, but is not limited to, Adriamycin, Alkeran, AntiVEGF monoclonal antibody SU5416, Aredia, Arimidex, BiCNU, Bleomycin, Blenoxane, Camptosar, Casodex, CeeNU, Celestone, CM101 Soluspan Suspension, CA1, Cerubidine, Cisplatin, Cosmegan, Cytosar U, Cytoxan, Daunorubricin, DaunoXome, Depo-Provera Sterile Aqueous Suspension, Didronel, Diethylstilbestrol, Diflucan, Doxil, Doxorubicin Hydrochloride, DTIC-Dome, Elspar, Emcyt, Epogen, Ergamisol, Ethyol, Etopophos, Etoposide, Eulexin, Femara, Fludara, Fluorouracil, Gemzar, Gliade, Hexylen, Hycamtin, Hydrea, Hydroxyurea, Idamycin, Iflex, Intron A, Kytril, Leucovorin Calcium, Leukeran, Leukine, Leustatin, Lupron, Lysodren, Marinol, Matulane, Mesnex, Methotrexate Sodium, Mithracin, Mitoxantrosc, Mustargen, Mutamycin, Myleran, Navelbine, Neupogen, Nilandron, Nipent, Nolvadex, Novantrone, Oncaspar, Oncovin, Paraplatin, Photofrin, Platinol, Procrit, Proleukin, Purinethol, Roferon A, Rubex, Salagen, Sandostatin, Squalamine, Sterile FUDR, Taxol, Taxotere, Teslac, Thalidomide, TheraCys BCG, Thioguanine, Thioplex, Tice BCG, TNP 470, Velban, Vesanoid, VePesid, Vitaxin, Vumon, Zanosar, Zinecard, Zofran, Zoladex, Zyloprim, and 2 Methoxy-oestradiol.

In some embodiments of the present application, a nanoparticle of a hepatic targeted drug delivery system comprising a carrier and an anticancer agent, wherein the carrier is a complex of polyethylene glycol (PEG) having a molecular weight of about 2,000-20,000 Da and a chitosan or a derivative thereof having a degree of deacetylation of above 70% and a molecular weight of about 3,000-200,000 Da, the carrier is modified with glycyrrhetinic acid.

In some embodiments of the present application, a nanoparticle of a hepatic targeted drug delivery system comprising a carrier and an anticancer agent, wherein the carrier is a complex of polyethylene glycol (PEG) having a molecular weight of about 2,000-20,000 Da and an alginate having a molecular weight of about 50,000-200,000 Da, the carrier is modified with glycyrrhetinic acid.

In some embodiments of the present application, a nanoparticle of a hepatic targeted drug delivery system comprising a carrier and an anticancer agent, wherein the carrier is a polyethylene glycol-poly(amino acid) ester and is modified with glycyrrhetinic acid, the polyethylene glycol is a diamine-terminal polyethylene glycol having a molecular weight of about 2,000 to 20,000 Da and the poly(amino acid) ester has a molecular weight of about 2,000 to 50,000 Da.

In some embodiments of the present application, a nanoparticle of a hepatic targeted drug delivery system comprising a carrier and an anticancer agent, wherein the carrier is a diamine-polyester and is modified with glycyrrhetinic acid, the polyethylene glycol is a diamine-terminal polyethylene glycol having a molecular weight of about 2,000 to 20,000 Da and the polyester has a molecular weight of about 2,000 to 50,000 Da.

In another aspect of the present application, there is a process for preparing a nanoparticle of a hepatic targeted drug delivery system comprising (a) modifying a carrier with glycyrrhetinic acid; and
(b) loading an anticancer agent to the carrier modified with glycyrrhetinic acid.

In some embodiments of the present application, the carrier used in the process is made of a biodegradable polymer.

In some preferred embodiments of the present application, a process for preparing a nanoparticle of a hepatic targeted drug delivery system comprising (a) modifying a carrier made of a complex of polyethylene glycol (PEG) and naturally occurring polysaccharide with glycyrrhetinic acid;
(b) loading an anticancer agent to the carrier modified with glycyrrhetinic acid; and
(c) adding an ion cross-linker into the resultant mixture.

Exemplary ion cross-linker that can be used in the present application includes, but is not limited to, sodium tripolyphosphate, sodium citrate, calcium chloride, calcium hydroxide, dextran sulfate and sodium poly(malic acid).

In some embodiments of the present application, an ion cross-linker is selected from the group consisting of sodium tripolyphosphate, sodium citrate, dextran sulfate and sodium poly(malic acid), where the carrier made of a complex of polyethylene glycol (PEG) and chitosan or derivatives thereof is modified with glycyrrhetinic acid.

In some embodiments of the present application, an ion cross-linker is selected from the group consisting of calcium chloride, and calcium hydroxide, where the carrier made of a complex of polyethylene glycol (PEG) and an alginate is modified with glycyrrhetinic acid.

In some embodiments of the present application, the molecular weight of dextran sulfate and sodium poly(malic acid) is in the range of about 2,000 to 8,000 Da.

In some more preferred embodiments of the application, the molar ratio of the glycyrrhetinic acid to the diaminopolyethylene glycol in step (a) is in the range of about 1 to 0.1-5.

In some more preferred embodiments of the application, the mass ratio of the naturally occurring polysaccharide to the glycyrrhetinic acid-poly(ethylene glycol) in step (a) is in the range of about 1 to 0.1-10.

In some more preferred embodiments of the application, the mass ratio of the naturally occurring polysaccharide to the anticancer agent in step (b) is in the range of about 1 to 0.1-2.

In some more preferred embodiments of the application, the mass ratio of the naturally occurring polysaccharide to the ion cross-linker in step (c) is in the range of about 1-8 to 1.

In some embodiments of the present application, a process for preparing a nanoparticle of a hepatic targeted drug delivery system comprising (a) preparing glycyrrhetinic acid-diaminopolyethylene glycol (GA-PEG) with glycyrrhetinic acid (GA) and diaminopolyethylene glycol (ATPEG);
(b) mixing GA-PEG, a naturally occurring polysaccharide and an anticancer agent to obtain a resultant mixture;
(c) adding an ion cross-linker into the resultant mixture to obtain a nanoparticle suspension; and
(d) centrifuging and lyophilizing the nanoparticles.

In some preferred embodiments of the present application, a process for preparing a nanoparticle of a hepatic targeted drug delivery system comprising (a) modifying a carrier made of a polyethylene glycol-poly(amino acid) ester with glycyrrhetinic acid; and
(b) loading an anticancer agent to the carrier modified with glycyrrhetinic acid.

In some more preferred embodiments of the application, the molar ratio of the glycyrrhetinic acid to the diaminopolyethylene glycol in step (a) is in the range of about 1 to 1-10.

In some more preferred embodiments of the application, the molar ratio of the glycyrrhetinic acid-polyethylene glycol to the N-carboxyanhydride monomer in step (a) is in the range of about 1 to 15-250.

In some embodiments of the present application, a process for preparing a nanoparticle of a hepatic targeted drug delivery system comprising (a) preparing glycyrrhetinic acid-diaminopolyethylene glycol (GA-PEG) with glycyrrhetinic acid (GA) and diaminopolyethylene glycol (ATPEG);

(b) mixing GA-PEG and N-carboxyanhydride (NCA) monomer to obtain glycyrrhetinic acid-polyethylene glycol-b-poly(amino acid) ester; and (c) loading an anticancer agent to the glycyrrhetinic acid-polyethylene glycol-b-poly(amino acid) ester to obtain a nanoparticle of a hepatic targeted drug delivery system.

In some preferred embodiments of the present application, a process for preparing a nanoparticle of a hepatic targeted drug delivery system further comprising (d) lyophilizing the resultant nanoparticle of a hepatic targeted drug delivery system.

In some preferred embodiments of the present application, an anticancer agent and glycyrrhetinic acid-polyethylene glycol-b-poly(amino acid)-ester are mixed in organic solvent and then dialyzed against a selective solvent to obtain a nanoparticle of a hepatic targeted drug delivery system, wherein the selective solvent is water, while the organic solvent is water-miscible, such as dimethylformamide, tetrahydrofuran, dimethylsulfoxide or a mixture thereof.

In some preferred embodiments of the present application, a process for preparing a nanoparticle of a hepatic targeted drug delivery system comprising (a) modifying a carrier made of diamine-polyester with glycyrrhetinic acid; and (b) loading an anticancer agent to the carrier modified with glycyrrhetinic acid.

In some more preferred embodiments of the application, the molar ratio of the glycyrrhetinic acid to the diamine in step (a) is in the range of about 1 to 1-50.

In some more preferred embodiments of the application, the molar ratio of the glycyrrhetinic acid-diamine to the polyester in step (a) is in the range of about 1 to 0.2-1.

In some preferred embodiments of the present application, a mixture of an anticancer agent and glycyrrhetinic acid-diamine-polyester is dialyzed against a selective solvent to obtain a nanoparticle of a hepatic targeted drug delivery system, wherein a selective solvent is water, while the organic solvent is water-miscible, such as dimethylformamide, tetrahydrofuran, dimethylsulfoxide or a mixture thereof.

In some preferred embodiments of the present application, a mixture of an anticancer agent and glycyrrhetinic acid-diamine-polyester is added in an organic solvent to give an organic phase and the resultant organic phase is added dropwise into an aqueous phase with stirring or with the aid of ultrasonic to obtain a nanoparticle of a hepatic targeted drug delivery system, wherein the organic solvent is selected from the group consisting of methylene chloride, acetone and tetrahydrofuran. In some embodiments of the present application, the aqueous phase is pure water or a solution containing polyvinyl alcohol (PVA), Tween 80, poloxamer 188, or poloxamer 407. In some preferred embodiments of the present application, the volume ratio of the organic phase to aqueous phase is in the range of about 1 to 5-50, while the content of polyvinyl alcohol, Tween 80, poloxamer 188, or poloxamer 407 in aqueous phase is in the range of about 0.1 to 5% by weight.

In some embodiments of the present application, a process for preparing a nanoparticle of a hepatic targeted drug delivery system comprising (a) preparing glycyrrhetinic acid-diamine with glycyrrhetinic acid (GA) and diamine;

(b) mixing GA-diamine and polyester to obtain glycyrrhetinic acid-diamine-polyester; and (c) loading an anticancer agent to the glycyrrhetinic acid-diamine-polyester to obtain a nanoparticle of a hepatic targeted drug delivery system.

In some preferred embodiments of the present application, a process for preparing a nanoparticle of a hepatic targeted drug delivery system further comprising (d) centrifuging and lyophilizing the resultant of a hepatic targeted drug delivery system.

Exemplary anticancer agent that can be used in the present application includes, but is not limited to, water-soluble anticancer agent including adriamycin hydrochloride, 5-fluorouracil, cytarabine hydrochloride, all-trans retinoic acid and cyclophosphamide; and water-insoluble or poorly water-soluble anticancer agent including anthracyclins, camptothecins, vinca alkaloids, paclitaxels, taxanes and cisplatin.

In another aspect of the present application, there is provided a pharmaceutical composition comprising a nanoparticle of a hepatic targeted drug delivery system and a pharmaceutically acceptable excipient, wherein the nanoparticle comprises a carrier and an anticancer agent and the carrier is modified with glycyrrhetinic acid.

The excipient used in the pharmaceutical compositions of the present application are those common types available in the pharmaceutical field, including binders, lubricants, disintegrants, solubilizers, diluents, stabilizers, suspending agents, colorants, flavouring agents and the like used in oral formulations; preservatives, solubilizers and stabilizers and the like used in injectable formulations; and substrates, diluents, lubricants and preservatives and the like used in focal formulations.

In another aspect of the present application, there is provided a method for treating liver cancer in a mammal comprising administering a therapeutically effective amount of nanoparticles of a hepatic targeted drug delivery system, wherein the nanoparticle comprises a carrier and an anticancer agent and the carrier is modified with glycyrrhetinic acid.

The term "therapeutically effective amount" as used herein refers to that amount of a nanoparticle of the invention or a pharmaceutical composition comprising the nanoparticle which, when administered to a mammal, preferably a human, is sufficient to effect treatment, as defined below, of a disease or condition of a liver cancer in the mammal, preferably a human. The amount of a nanoparticle of the invention or a pharmaceutical composition comprising the nanoparticle which constitutes a "therapeutically effective amount" will vary depending on the nanoparticle or the pharmaceutical composition comprising the nanoparticle, the condition and its severity, and the age of the mammal to be treated, but can be determined routinely by one of ordinary skill in the art having regard to his own knowledge and to this disclosure.

The term "treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

The term "liver cancer" as used herein refers to both primary liver cancer and secondary liver cancer. Primary liver cancer is cancer that originated in the tissues of the liver. Secondary liver cancer is cancer that spreads to the liver from another part of the body, most commonly from the cancers of bowel, pancreas, stomach, lung or breast. The behaviour, treatment and outlook of the two kinds of liver cancer are quite different from each other.

The symptoms in the early stage of the primary liver cancer is quite vague and non-specific, like feeling generally unwell, sick (nausea), off food, weight loss and tiredness, sometime even associate with cirrhosis. As the cancer grows, more specific symptoms may also develop including abdominal pain over the liver area, jaundice and itch.

Compared with the primary liver cancer, the symptoms of the second liver cancer is a bit mild, such as feeling tired, general hyperhidrosis.

EXAMPLES

Embodiments of the present application are disclosed in further detail in the following examples, which are not in any way intended to limit the scope of the application.

Reagents and Apparatus

| Reagents/Apparatus | Available Sources |
|---|---|
| glycyrrhetinic acid | Fujie Pharmaceutical Limited Company (Xi'an, China) |
| DCC | GL Biochem (Shanghai, China) |
| NHS | GL Biochem (Shanghai, China) |
| DMAP | GL Biochem (Shanghai, China) |
| diaminopolyethylene glycol | Fluka Chemie (Buchs, Switzerland)/ Sigma Chem Co. (St. Louis, MO) |
| FITC | Qianchen Biological science and technology Limited Company (Shanghai, China) |
| 5-fluorouracil | Nanjing KeyGen Biotech. Co. Ltd |
| hydroxyl camptothecin (HCPT) | ShellGene Biotech. Co. Ltd (Shanghai, China) |
| Paclitaxel | TongChen Biotech. Co. Ltd (Shanghai, China) |
| doxorubicin | Huafeng United Technology Co (Beijing, China) |
| poly(lactide-co-glycolide) (PLGA) | Daigang Biology. Co. Ltd (Ji'nan, China) |
| Polycaprolactone (PCL) | Daigang Biology. Co. Ltd (Ji'nan, China) |
| Polylactide (PLA) | Daigang Biology. Co. Ltd (Ji'nan, China) |
| CTS | Yuhuan Ocean Biochemical Company (Zhejiang, China) |
| NMR | Varian UNITY-PLUS 400 NMR Spectrometer |
| TEM | Technai $G^2$ 20-S-TWIN microscope |
| UV-Vis | Unico 4802 UV-Vis Spectrophotometer |
| HPLC | Waters, Milford, MA, USA |
| Centrifuge | Sigma 3K-30 |
| PCS | BI-9000AT, Brookhaven Co. USA |
| bag filter | Green Bird Science and Technology Development Co., Ltd (Shanghai, China) |

Examples 1-7

Preparation Of Glycyrrhetinic Acid-Modified Diamine

Example 1

Preparation of Glycyrrhetinic Acid-Ethylenediamine

To N,N'-dimethylformamide (10 mL) were added glycyrrhetinic acid (1.0 mmol, 0.474 g) and ethylenediamine (30.0 mmol, 1.8 g, 2.0 mL). To the obtained solution were added dicyclohexyl carbodiimide (1.2 mmol, 0.247 g) and 4-N,N'-dimethylaminopyridine (catalytic amount) at 0° C. The mixture was stirred for 0.5-1 hour at 0° C. and then refluxed for further 12-48 hours. The resultant solution was filtered. To the filtrate was dropwise added diethyl ether. The precipitate was recovered and dried under vacuum to give glycyrrhetinic acid-ethylenediamine (yield=92%).

Example 2

Preparation of Glycyrrhetinic Acid-1,3-Propanediamine

Glycyrrhetinic acid-1,3-propanediamine was prepared according to the substantially same method as described in Example 1, except that 1,3-propanediamine (30.0 mmol, 2.22 g) was used instead of ethylenediamine (yield=90%).

Example 3

Preparation of Glycyrrhetinic Acid-Hexanediamine

Glycyrrhetinic acid-hexanediamine was prepared according to the substantially same method as described in Example 1, except that hexanediamine (30.0 mmol, 3.48 g) was used instead of ethylenediamine (yield=89%).

Example 4

Preparation of Glycyrrhetinic Acid-Diaminopolyethylene Glycol ($M_w$=2,000 Daltons)

To methylene chloride (15 mL) were added glycyrrhetinic acid (1.0 mmol, 0.474 g) and diaminopolyethylene glycol (5.0 mmol, 10 g, $M_w$=2,000 Daltons). To the obtained solution were added dicyclohexyl carbodiimide (1.2 mmol, 0.247 g) and 4-N,N'-dimethylaminopyridine (catalytic amount) at 0° C. The mixture was stirred for 0.5-1 hour at 0° C. and then refluxed for further 12-48 hours. The resultant solution was filtered. To the filtrate was dropwise added diethyl ether. The precipitate was recovered and dried under vacuum to give glycyrrhetinic acid-diaminopolyethylene Glycol (GA-$PEG_{2000}$) (yield=85%).

Example 5

Preparation of Glycyrrhetinic Acid-Diaminopolyethylene Glycol ($M_w$=3,400 Daltons)

Glycyrrhetinic acid-diaminopolyethylene glycol ($M_w$=3,400 Daltons) was prepared according to the substantially same procedures as described in Example 4 except that diaminopolyethylene glycol ($M_w$=3,400 Daltons) was used instead of diaminopolyethylene glycol ($M_w$=2,000 Daltons) (yield=87%).

The condensation reaction of glycyrrhetinic acid with diaminopolyethylene glycol was confirmed by the proton nuclear magnetic resonance ($^1$H NMR). The results were shown in FIG. 1, in which the chemical shifts from 0.64 to 1.8 ppm were the protons of methyl and methane groups of glycyrrhetinic acid, while the peak at 3.64 ppm was attributed to the —CH$_2$— protons of PEG block.

Example 6

Preparation of Glycyrrhetinic Acid-Diaminopolyethylene Glycol ($M_w$=6,000 Daltons)

Glycyrrhetinic acid-diaminopolyethylene glycol ($M_w$=6,000 Daltons) was prepared according to the substantially same procedures as described in Example 4 except that diaminopolyethylene glycol ($M_w$=6,000 Daltons) was used instead of diaminopolyethylene glycol ($M_w$=2,000 Daltons) (yield=86%).

Example 7

Preparation of Glycyrrhetinic Acid-Diaminopolyethylene Glycol ($M_w$=10,000 Daltons)

Glycyrrhetinic acid-diaminopolyethylene glycol ($M_w$=110,000 Daltons) was prepared according to the substantially same procedures as described in Example 4 except that diaminopolyethylene glycol ($M_w$=10,000 Daltons) was used instead of diaminopolyethylene glycol ($M_w$=2,000 Daltons) (yield=85%).

Example 8

Figure 2:
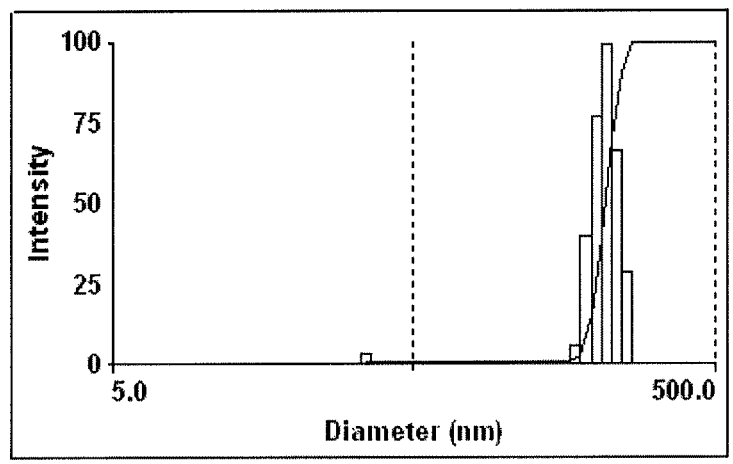
FIG. 2 illustrates (a) the particle size distribution and (b) the morphology of GA-PEG/CTS complex nanoparticles prepared in Example 8.
Figure 2:
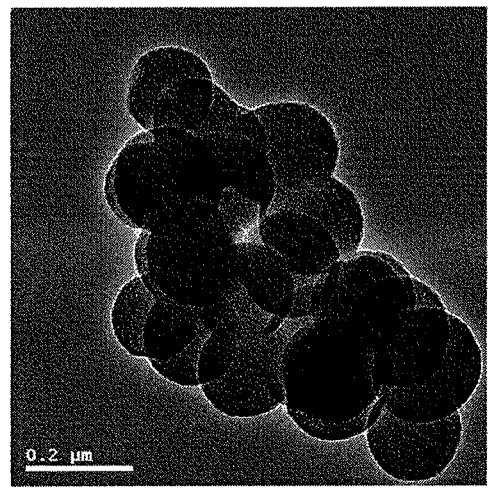

Preparation of Nanoparticles of Hepatic Targeted Drug Delivery System Based on Glycyrrhetinic Acid-Polyethylene Glycol/Natural Polysaccharide Complex Preparation of nanoparticles based on glycyrrhetinic acid-polyethylene glycol/chitosan complex Preparation of mixture solution
To hydrochloric acid (5.0 mL, 1%) were added chitosan (8.75 mg, Mw=50,000 Daltons, degree of deacetylation=95%) and GA-PEG$_{3400}$ (7.0 mg) prepared in Example 5 to give a mixture solution. The concentrations of chitosan and GA-PEG$_{3400}$ were 1.75 mg/mL and 1.4 mg/mL, respectively.
Preparation of ion cross-linker solution
Aqueous sodium tripolyphosphate solution (1.0 mg/mL) was prepared according to the conventional method in the art.
Preparation of nanoparticles based on glycyrrhetinic acid-polyethylene glycol/chitosan complex
To the mixture solution (5.0 mL) was added the ion cross-linker solution (2.0 mL) at a rate of 0.5-1 mL/min with strongly stirring to give a nanoparticle suspension. Laser light scattering (90-PLUS analyzer, Brookhaven) and transmission electron microscopy were used to observe the particle size and morphology of the complex nanoparticles. As shown in FIGS. 2a and 2b, the particle size of the prepared nanoparticles were about 210±5 nm with a regular spherical shape.
Determination of the content of glycyrrhetinic acid in the complex nanoparticles
A desired amount of the nanoparticles prepared in the previous step were dissolved in hydrochloric acid. The absorbance was measured with UV-Vis at 252 nm and the weight percent of glycyrrhetinic acid was 4.5% according to the standard curve.

In Vitro Release Profile of Doxorubicin-Loaded Nanoparticles Based on Glycyrrhetinic Acid-Polyethylene Glycol/Chitosan Complex Preparation of mixture solution containing doxorubicin
To hydrochloric acid (5.0 mL 1%) were added chitosan (8.75 mg, $M_w$=50,000 Daltons, degree of deacetylation=95%), of GA-PEG$_{6000}$ prepared in Example 6 (7.0 mg) and doxorubicin hydrochloride (3.0 mg) to give a mixture solution containing doxorubicin. The concentrations of chitosan and GA-PEG$_{6000}$ were 1.75 mg/mL and 1.4 mg/mL, respectively.
Preparation of doxorubicin-loaded nanoparticles
Doxorubicin-loaded nanoparticles were prepared with the similar process as described in Preparation of Nanoparticles Based on Glycyrrhetinic Acid-Polyethylene Glycol/Chitosan Complex. The doxorubicin-loaded nanoparticles has an effective particle size of about 216 nm measured by photo correlation spectroscopy and a polydispersity of 0.205.
Determination of Encapsulation Efficiency (Ee) And Loading Capacity (LC) of the doxorubicin-loaded nanoparticles
To determine the encapsulation efficiency and loading capacity, samples of the doxorubicin-loaded nanoparticles were centrifuged at 24000×g for 20 min, and then the pellets were lyophilized and weighted. The DOX concentration in supernatant was calculated by reversed phase HPLC on a C18 column (250 mm×4.6 mm). The mobile phase was a mixture of methanol/acetic acid (80:20, v/v). EE and LC were calculated based on the following equations:

$$EE = \frac{\text{weight of } doxorubicin \text{ in the nanoparticles}}{\text{weight of the feeding } doxorubicin} \times 100\% \quad (1)$$

$$LC = \frac{\text{weight of } doxorubicin \text{ in the nanoparticles}}{\text{weight of the nanoparticles}} \times 100\% \quad (2)$$

Figure 3:
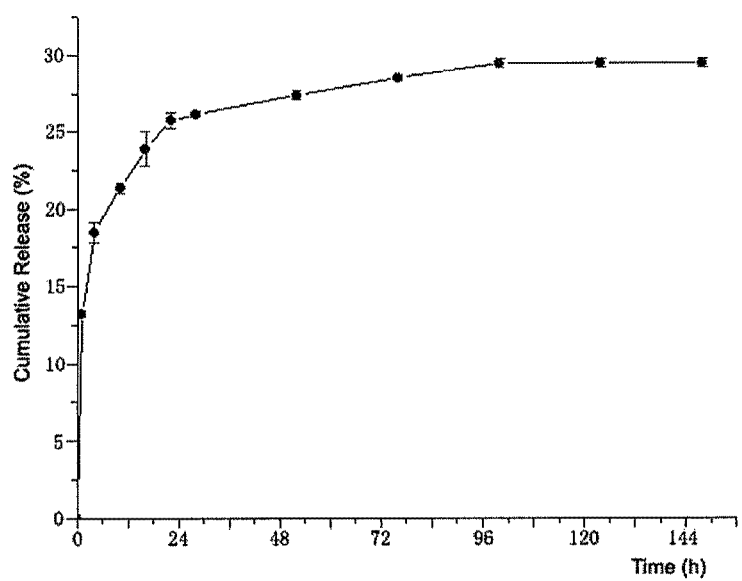
FIG. 3 illustrates the in vitro release profiles of doxorubicin-loaded GA-PEG/CTS complex nanoparticles prepared in Example 8.

EE and LC values of the doxorubicin-loaded nanoparticles were 50.2% and 5.0%, respectively.
In vitro release study of doxorubicin-loaded nanoparticles
For drug release studies, a desired amount of lyophilized doxorubicin-loaded nanoparticles were suspended in PBS (10 mL, pH 7.4). The suspension was continuously shaken at a speed of about 90±5 rpm·min$^{-1}$ at 37° C. At scheduled time intervals, supernatants were isolated by centrifugation. The medium was removed for HPLC analysis and replaced by fresh PBS.
The doxorubicin-loaded nanoparticles showed an initial burst release of 13% during the first two hours and a cumulative release percentage of 28% over the next six days. The release profiles were shown in FIG. 3.

In Vitro Cell Uptake of Complex Nanoparticles Based on Glycyrrhetinic Acid-Polyethylene Glycol/Chitosan Complex Preparation of FITC-labeled chitosan (FITC-CTS)
FITC-labeled chitosan was synthesized based on the reaction between isothiocyanate group of FITC and primary amino groups of chitosan. Briefly, to FITC (5.5 mg) in methanol (10 mL) was added chitosan (5.5 mL, 1%, $M_w$=50,000 Daltons, degree of deacetylation=95%). The reaction was carried out for 24 hours in the dark. To the reaction system was added aqueous sodium hydroxide to adjust the pH to be weakly alkaline. The precipitate was recovered by centrifugation and resolved with hydrochloric acid (1%). The mixture was dialyzed against distilled water using a cellulose membrane (cutoff=12,000) for three days. The dialyzed solution was lyophilized to give the FITC-labeled chitosan as a fluffy sponge. A desired amount of the lyophilized product was dissolved in hydrochloric acid to give a solution with a concentration of 1.75 mg/mL.

Preparation of FITC-labeled nanoparticles

The FITC-labeled nanoparticles were prepared with FITC-CTS and GA-PEG$_{3400}$ according to the method described in Preparation of Nanoparticles Based on Glycyrrhetinic Acid-Polyethylene Glycol/Chitosan Complex.

In vitro cell uptake of nanoparticles

The FITC-labeled nanoparticles were filtered through a 0.45-μm membrane for sterilization. Subsequently, 200 μL of the labeled nanoparticles were added to A549 (human lung carcinoma cells), LO2 (human normal liver cells) and 7703 (human hepatic carcinoma cells), respectively, which were pre-cultured in 96-well plates. After incubation for four hours, the mixture was washed twice with RPMI 1640 and the fluorescence images were obtained by fluorescence microscopy (Olympus, Tokyo, Japan).

Figure 4:
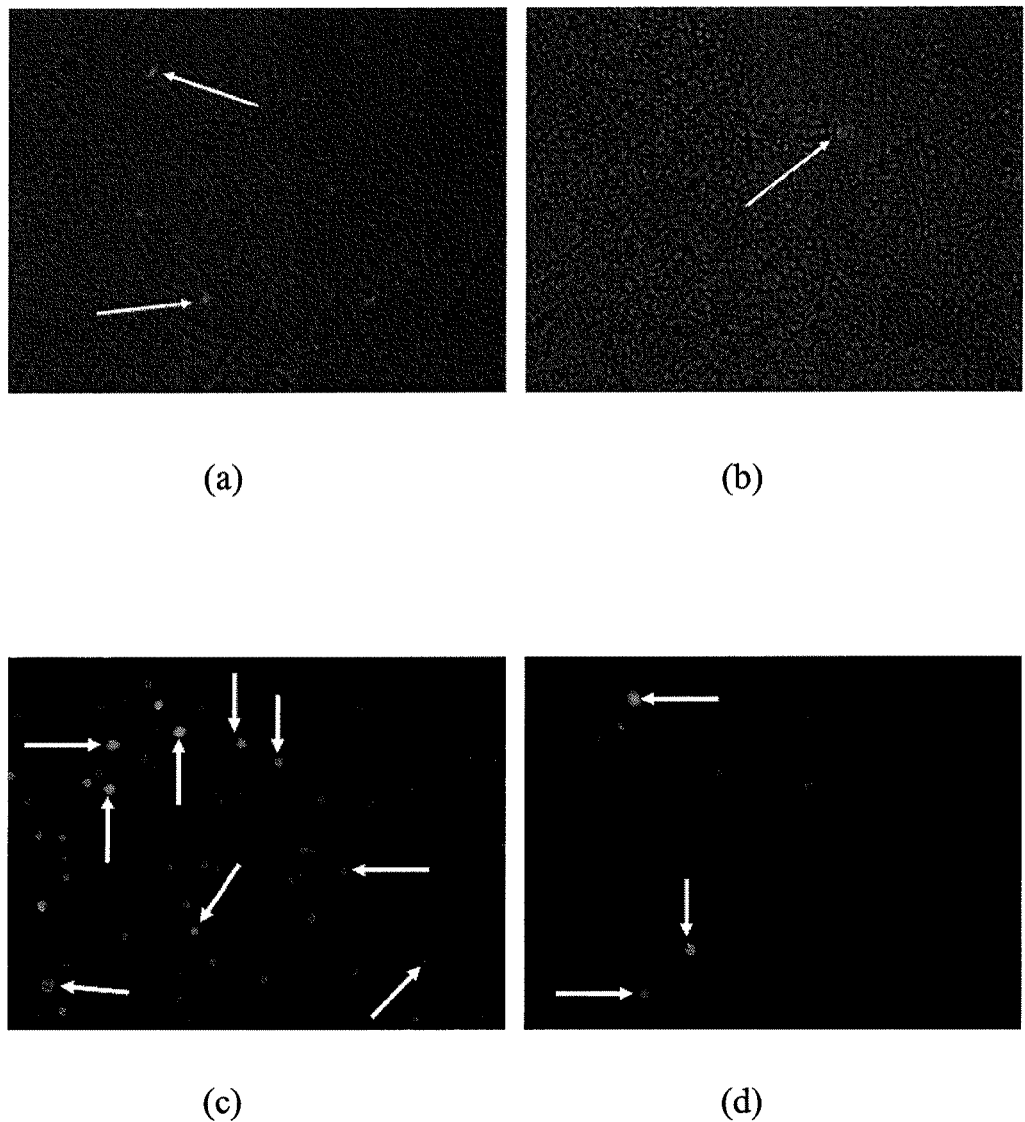
FIG. 4 illustrates the fluorescence images of different cancer cells ((a) 7703 hepatic carcinoma cells (b) A549 lung carcinoma cells) treated with PEG/CTS nanoparticles and the fluorescence images of different liver cells ((c) 7703 hepatic carcinoma cells (d) LO2 normal hepatic cells) treated with GA-PEG/CTS nanoparticles prepared in Example 8.

The results were shown in FIG. 4, in which very little and weak fluorescences were observed in both 7703 cells and A549 cells after incubating with the nanoparticles without modified glycyrrhetinic acid during the same period. On the contrary, much stronger fluorescence was observed in 7703 cells incubated with the nanoparticles modified with glycyrrhetinic acid. More specially, the fluorescence intensity of 7703 cells was stronger than LO2 cells. These results indicated that the nanoparticles bearing glycyrrhetinic acid residue could be taken up by hepatic cancer cells via ligand-receptor recognition.

Preparation of 5-Fluorouracil-Loaded Nanoparticles Based on Glycyrrhetinic Acid-Polyethylene Glycol/Chitosan Complex Preparation of mixture containing 5-fluorouracil To hydrochloric acid (1%, 5.0 mL) were added glycol chitosan (8.75 mg, M$_w$=50,000 Daltons, degree of deacetylation=95%), GA-PEG$_{6000}$ (7.0 mg) prepared in Example 6 and of 5-fluorouracil (3.0 mg). The concentrations of glycol chitosan and GA-PEG$_{6000}$ were about 1.75 mg/mL and 1.4 mg/mL, respectively.

Preparation of complex ion cross-linker solution

To distilled water (2.0 mL) were added of sodium tripolyphosphate (2.0 mg) and dextran sulfate (1.875 mg, M$_w$=4,000 Daltons) to give an ion cross-linker solution.

Preparation of 5-fluorouracil-loaded nanoparticles

To the mixture containing 5-fluorouracil (5.0 mL) prepared above was added the ion cross-linker solution (2.0 mL) at a rate of 0.5-1 mL/min with strongly stirring to give a nanoparticle suspension. The average particle size of the 5-fluorouracil-loaded nanoparticles was about 225 nm measured by PCS.

Determination of the encapsulation efficiency (EE) and loading capacity (LC)

To determine the encapsulation efficiency and loading capacity, samples were centrifugated at 24000×g for 20 min, and then the pellets were lyophilized and weighted. The concentration of 5-fluorouracil in the supernatant was measured by UV at 266 nm. EE and LC values were calculated based on the following equations:

$$EE = \frac{\text{weight of 5-}\textit{fluorouracil}\text{ in the nanoparticles}}{\text{weight of the feeding 5-}\textit{fluorouracil}} \times 100\% \quad (3)$$

$$LC = \frac{\text{weight of 5-}\textit{fluorouracil}\text{ in the nanoparticles}}{\text{weight of the nanoparticles}} \times 100\% \quad (4)$$

The EE and LC values of the 5-fluorouracil-loaded nanoparticles were 65.4% and 10.5%, respectively.

Preparation of Nanoparticles of Hepatic Targeted Drug Delivery System Based on Glycyrrhetinic Acid-Polyethylene Glycol/Alginate Complex Preparation of Nanoparticles Based on Glycyrrhetinic Acid-Polyethylene Glycol/Alginate Complex Preparation of mixture solution Alginate (5.0 mg, Mw=50,000 Daltons) and GA-PEG$_{10000}$ (5.0 mg) prepared in Example 7 were mixed together in aqueous solution. The concentrations of alginate and GA-PEG$_{10000}$ were both 1.0 mg/mL.

Preparation of ion cross-linker solution

Aqueous calcium chloride solution (1.0 mg/mL) was prepared according to the conventional method in the art.

Preparation of nanoparticles based on glycyrrhetinic acid-polyethylene glycol/alginate complex To the mixture solution (5.0 mL) was added the ion cross-linker solution (2.0 mL) at a rate of 0.5-1 mL/min with strongly stirring to give a nanoparticle suspension. Nanoparticles were obtained after centrifugation.

Preparation of drug loaded nanoparticles based on glycyrrhetinic acid-polyethylene glycol/alginate complex To the mixture solution (5.0 mL) was added alginate (5.0 mg, Mw=50,000 Daltons), of GA-PEG$_{1000}$ prepared in Example 7 (5.0 mg) and doxorubicin hydrochloride (3.0 mg) to give a mixture solution containing doxorubicin. Then the aqueous calcium chloride solution (1.0 mg/mL, 2.0 mL) was added to give a nanoparticle suspension. The particle size of doxorubicin-loaded nanoparticles was about 386 nm measured by photo correlation spectroscopy.

Example 9

Preparation of Nanoparticles of Hepatic Targeted Drug Delivery System Based on Glycyrrhetinic Acid-Polyethylene Glycol-b-Poly(Amino Acid) Ester Block Copolymers Preparation of Nanoparticles Based on Glycyrrhetinic Acid-Polyethylene Glycol-Poly(Amino Acid) Ester Block Copolymers Preparation of glycyrrhetinic acid-polyethylene glycol-b-poly(γ-benzyl-L-aspartate block copolymers (GA-PEG-PBLA)

The block copolymer of glycyrrhetinic acid-polyethylene glycol-b-poly(γ-benzyl-L-aspartate) was prepared by the ring opening polymerization of γ-benzyl-L-aspartate N-carboxyanhydride (BLA-NCA) initiated by glycyrrhetinic acid-di-aminopolyethylene glycol.

To a reaction bottle were added N,N'-dimethylformamide (DMF) (250 mL), GA-PEG$_{2000}$ (1 mmol, 2.47 g) prepared in Example 4 and BLA-NCA (50 mmol, 12.45 g) at room temperature. The mixture was stirred under nitrogen for 48 hours.

The reaction mixture was precipitated with diethyl ether. The precipitate was filtered and dried under vacuum to give glycyrrhetinic acid-polyethylene glycol$_{2000}$-b-poly(γ-benzyl-L-aspartate) abbreviated as GA-PEG$_{2000}$-PBLA (yield=78%).
Preparation of glycyrrhetinic acid-polyethylene glycol-b-poly(γ-benzyl-l-glutamate) block copolymer (GA-PEG-PBLG)

The block copolymer of glycyrrhetinic acid-polyethylene glycol-b-poly(γ-benzyl-L-glutamate) was prepared according to the substantially same method as described in the preparation of GA-PEG$_{2000}$-PBLA, except that GA-PEG$_{3400}$ prepared in Example 5 (1 mmol, 3.87 g) and γ-benzyl-L-glutamate N-carboxyanhydride (BLG-NCA) (20 mmol, 5.26 g) and DMF (120 mL) were used. Glycyrrhetinic acid-polyethylene glycol$_{3400}$-b-poly(γ-benzyl-L-glutamate) abbreviated as GA-PEG$_{3400}$-PBLG was obtained (yield=72%).

Figure 5:
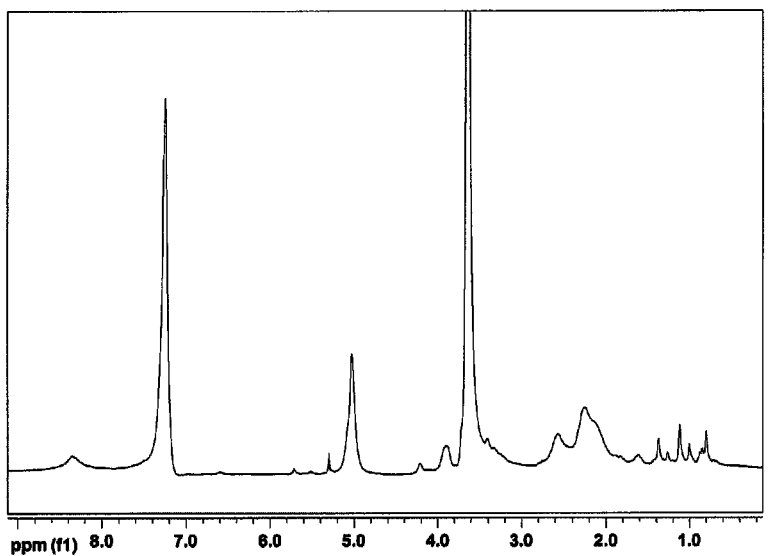
FIG. 5 illustrates $^1$H NMR spectrum of GA-PEG-PBLG block copolymer prepared in Example 9.

The polymerization reaction was confirmed by the proton nuclear magnetic resonance. The $^1$H NMR spectrum of GA-PEG-PBLG was shown in FIG. 5. Typical signals of both PEG and PBLG units were detected. The peaks at 8.37, 7.27, 5.05, 3.94 and 1.95-2.62 ppm were characteristic proton peaks of PBLG segments while the peak at 3.66 ppm was assigned to the protons of PEG units. In addition, the peaks from 0.64 to 1.8 ppm were the characteristic proton peaks of glycyrrhetinic acid.

Figure 6:
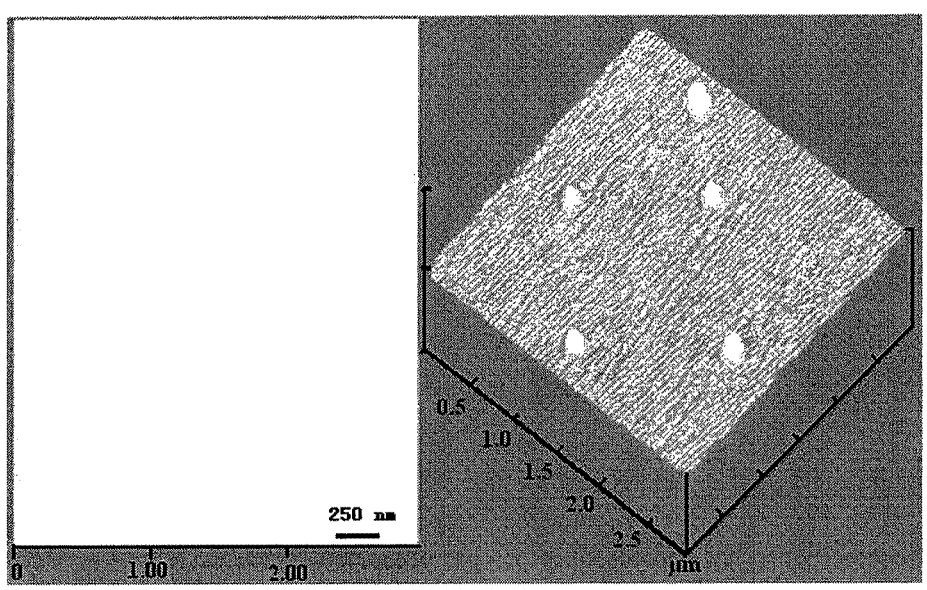
FIG. 6 illustrates the morphology of hydroxyl camptothecin-loaded GA-PEG-PBLA nanoparticles prepared in Example 9 acquired by atomic force microscopy (AFM).

Preparation of Nanoparticles Based on Glycyrrhetinic Acid-Polyethylene Glycol-Poly(Amino Acid) Ester Preparation of nanoparticles of hepatic targeted drug delivery system based on GA-PEG-PBLA To a mixture of tetrahydrofuran (THF) and N,N'-dimethylformamide (DMF) (3:7, v/v) were added hydroxyl camptothecin (HCPT) (15 mg) and GA-PEG$_{2000}$-PBLA (30 mg) prepared previously according to the procedures disclosed in the present application. The resultant solution was extensively dialyzed against distilled water for 2 days to remove unencapsulated HCPT and the organic solvent. Atomic force microscopy (AFM) was used to investigate the morphology and particle size distribution. As shown in FIG. 6, the nanoparticles were spherical in shape with a smooth surface and the particle size ranged from 230 to 250 nm.

Figure 7:
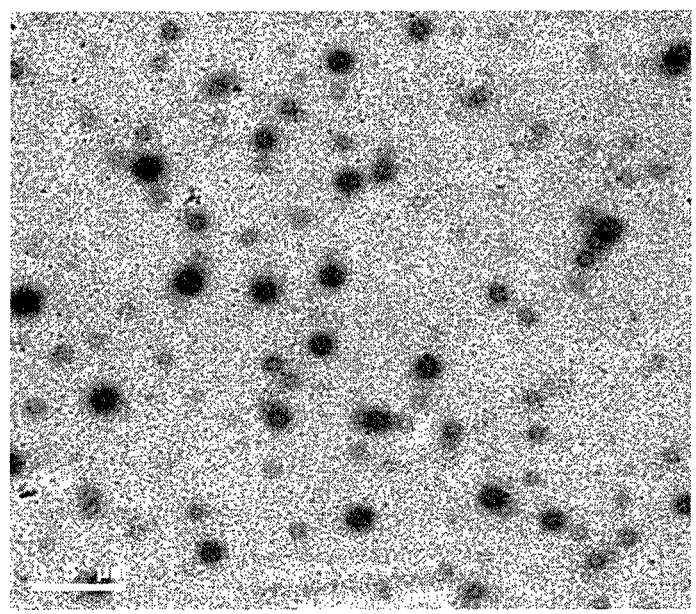
FIG. 7 illustrates the morphology of doxorubicin-loaded GA-PEG-PBLG nanoparticles prepared in Example 9 acquired by transmission electron microscopy (TEM).

Preparation of nanoparticles of hepatic targeted drug delivery system based on GA-PEG-PBLG To DMF (20 mL) were added doxorubicin (20 mg), triethylamine (10 mg) and GA-PEG$_{3400}$-PBLG (30 mg) prepared previously according to the procedures disclosed in the present application. The resultant mixture was extensively dialyzed against distilled water to remove unencapsulated doxorubicin and the organic solvent. The morphology and particle size of the prepared nanoparticles were observed by transmission electron microscopy (TEM) and shown in FIG. 7, exhibiting regular spherical shape and a particle size ranging from 185 to 200 nm.

In Vitro Release Study of Doxorubicin-Loaded Nanoparticles

Preparation of doxorubicin-loaded GA-PEG$_{3400}$-PBLG nanoparticles

Doxorubicin-loaded GA-PEG$_{3400}$-PBLG nanoparticles were prepared according to the procedures described in the present application.

Preparation of blank GA-PEG$_{3400}$-PBLG nanoparticles

Blank GA-PEG$_{3400}$-PBLG nanoparticles were prepared according to the procedures of preparation of doxorubicin-loaded nanoparticles, except that no doxorubicin was added.

Determination of doxorubicin encapsulation efficiency (ee) and loading capacity (LC)

The content of doxorubicin in the nanoparticles was measured by UV at 480 nm, while the prepared blank nanoparticles were used as a blank control. To determinate the encapsulation efficiency (EE) and loading capacity (LC), samples were centrifugated and the pellets were lyophilized and weighted. EE and LC values were calculated based on the equations (1) and (2).

The EE and LC values of the doxorubicin-loaded nanoparticles were 70.5% and 30.8%, respectively.

In vitro release study

Figure 8:
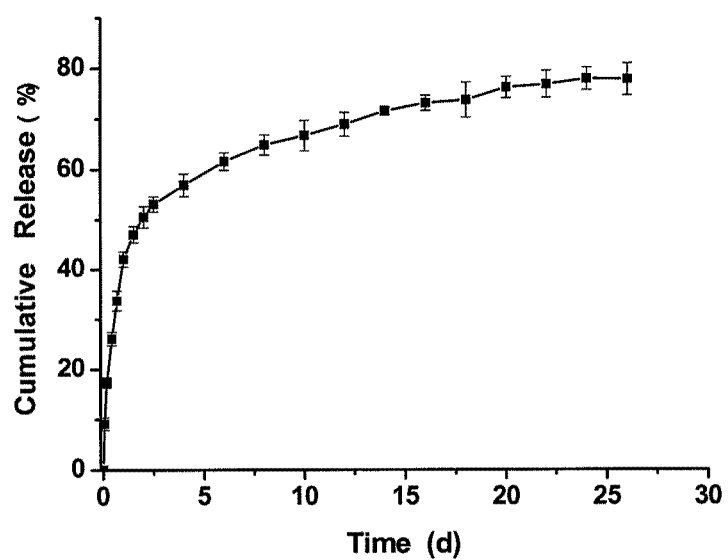
FIG. 8 illustrates the in vitro release profiles of doxorubicin from GA-PEG-PBLG nanoparticles prepared in Example 9.

The in vitro release study was performed according to the method described in in vitro release study of doxorubicin-loaded nanoparticles. As shown in FIG. 8, the release behavior of doxorubicin from the prepared nanoparticles exhibited a biphasic pattern characterized by an initial burst release during the first two days, followed by a slower and continuous release during the last 24 days. The cumulative release rate is up to 80.93%.

Stability Study of GA-PEG-PBLG nanoparticle

The steric stability of nanoparticle suspension is primarily important for clinical administration. GA-PEG$_{3400}$-PBLG nanoparticles prepared in the present application exhibits a core-shell structure. The hydrophobic PBLG segment comprises the compact core while the hydrophilic PEG segment extends to the outer aqueous environment and presents as a hydrophilic polymeric brush on the surface of polymeric micelles which may enhance the stability of nanoparticles.

Figure 9:
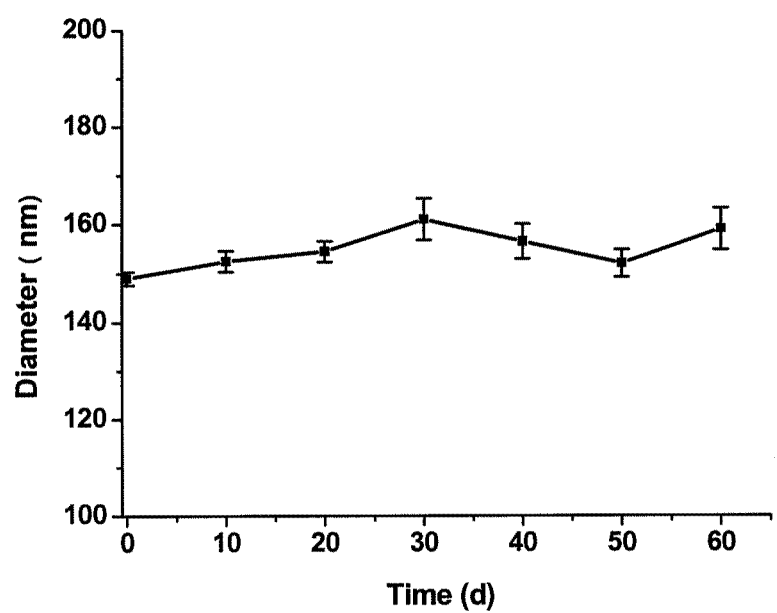
FIG. 9 illustrates the stability of GA-PEG-PBLG nanoparticles prepared in Example 9.

The in vitro stability study was carried out as follows: a certain concentration of the nanoparticles was withdrawn and the particle size was recorded at particular time intervals. The results were shown in FIG. 9, no aggregation or precipitation was observed during storage for up to more than two months.

Biodistribution of GA-PEG-PBLG nanoparticles in Wistar rats

Figure 10:
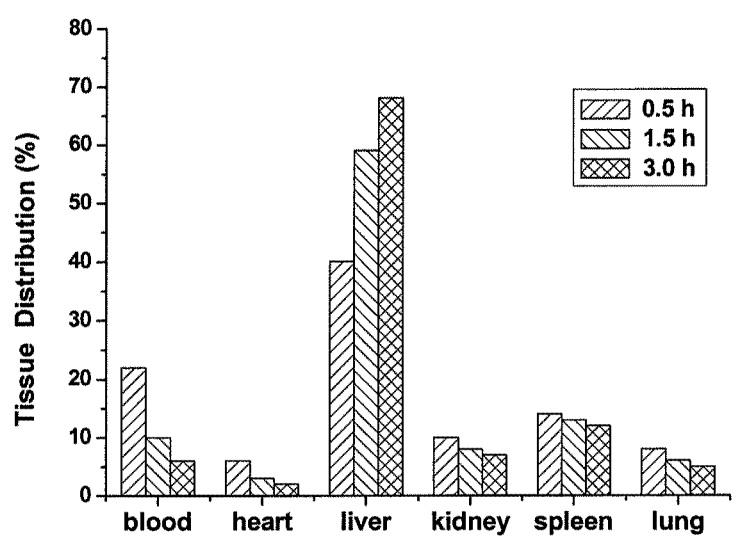
FIG. 10 illustrates the tissue distribution in Wistar rats of GA-PEG-PBLG nanoparticles loaded with rhodamine B prepared in Example 9.

In the study, Rhodamine B was used as a model fluorescent probe that can be encapsulated into the hydrophobic core of GA-PEG$_{3400}$-PBLG nanoparticles prepared in the present application. The Rhodamine B-loaded nanoparticles were dispersed in aqueous NaCl (0.9%) and injected intravenously into the tail veins of rats (500 μL of solution to each rat). The rats were sacrificed at different time intervals. Blood was collected. Various tissues including blood, heart, lung, liver, spleen and kidney were excised, washed with aqueous NaCl (0.9%) to remove the remaining Rhodamine B and accurately weighed. The samples were homogenized and centrifugated for 15 min. Methanol was added to the supernatant, followed by centrifugation. Finally, the fluorescence intensities of the solution were measured using a spectrofluorometer at an excitation wavelength of 540 nm and an emission wavelength of 580 nm. The results were expressed as a percentage of dosage for each organ and shown in FIG. 10.

Example 10

Preparation of Nanoparticles of Hepatic Targeted Drug Delivery System Based on Glycyrrhetinic Acid-Diamine-Polyesters Preparation of Glycyrrhetinic Acid-Diamine-Polyesters Preparation of glycyrrhetinic acid-ethylenediamine-poly(lactide-co-glycolide)

To methylene chloride (40 mL) were added poly(lactide-co-glycolide) (PLGA) (0.5 mmol, 6 g, $M_w$=12,000 Daltons), DCC (1.2 mmol, 0.24 g) and NHS (1.2 mmol, 0.14 g) (molar ratio of PLGA:DCC:NHS=1:1.2:1.2) at room temperature. The reaction was carried out under nitrogen for 15 hours. The resultant solution was filtered to remove the by-product dicycohexylurea (DCU). Anhydrous diethyl ether was added into the filtrate. The precipitate was recovered and dried under vacuum to give an activated PLGA as a white solid (yield=86%).

The condensation reaction was conducted as follows. To DMSO (60 mL) were added glycyrrhetinic acid-modified ethylenediamine (1 mmol, 0.516 g) prepared in the present application and activated PLGA (1 mmol, 1.2 g). The reaction mixture was stirred at room temperature for two days under nitrogen and then concentrated. Anhydrous methanol was added to the concentrate. The precipitate was recovered and dried under vacuum to give glycyrrhetinic acid-ethylenediamine-poly(lactide-co-glycolide) (yield=80%).

Preparation of glycyrrhetinic acid-polyethylene glycol-polycaprolactone block copolymer (GA-PEG-PCL)

Polycaprolactone (PCL, $M_w$=8,000 Daltons) was activated by DCC and NHS in methylene chloride according to the substantially same process described above.

The condensation reaction was conducted as follows. To dimethylsulfoxide (DMSO) (80 mL) were added GA-PEG$_{3400}$ (1 mmol, 3.87 g) prepared in Example 5 and activated polycaprolactone (1 mmol, 8 g). The reaction mixture was stirred at room temperature for two days under nitrogen and then concentrated. Anhydrous methanol was added to the concentrate. The precipitate was recovered and dried under vacuum to give glycyrrhetinic acid-polyethylene glycol-polycaprolactone (yield=84%).

Preparation of glycyrrhetinic acid-polyethylene glycol-poly(lactide-co-glycolide block copolymer (GA-PEG-PLGA)

GA-PEG-PLGA block copolymer was prepared according to the substantially same method as described in the preparation of GA-PEG-PCL, except that DMSO, GA-PEG$_{6000}$ and activated PLGA$_{12000}$ were used.

Figure 11:
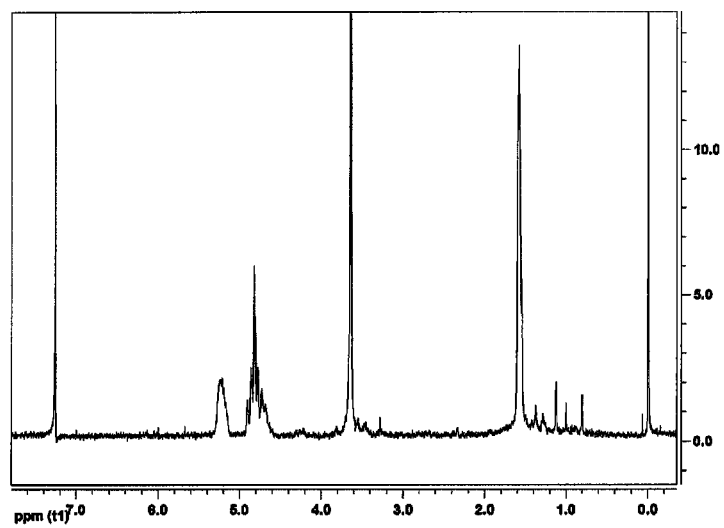
FIG. 11 illustrates $^1$H NMR spectrum of GA-PEG-PLGA block copolymer prepared in Example 10.

As shown in FIG. 11, the condensation reaction was confirmed by the $^1$H NMR spectrum of GA-PEG-PLGA. The peak at 3.6 ppm was attributed to the —CH$_2$— protons of PEG block. The peaks at 5.2 ppm and 1.6 ppm originated from —CH— protons and —CH$_3$ protons of the PLA block while the peak at 4.8 ppm belonged to the —CH$_2$— protons of PGA block. The small peaks ranged from 0.64 to 1.80 ppm were the typical protons of glycyrrhetinic acid.

Preparation of Nanoparticles of Hepatic Targeted Drug Delivery System Based on Glycyrrhetinic Acid-Diamine-Polyesters Preparation of paclitaxel-loaded GA-ethylenediamine-PLGA nanoparticles Paclitaxel-loaded nanoparticles were prepared using solvent evaporation technique. To acetone (5 mL) were added paclitaxel (5 mg) and of GA-ethylenediamine-PLGA (15 mg) prepared in the present application at room temperature. The resultant mixture was dropwise added into an aqueous poly (vinyl alcohol) solution (2%, W/V). Acetone was completely removed under reduced pressure. The resulting nanoparticle suspension was filtered through a 0.45-μm membrane and then stored at 4° C.

Preparation of doxorubicin-loaded GA-PEG$_{6000}$-PLGA Nanoparticles

Figure 12:
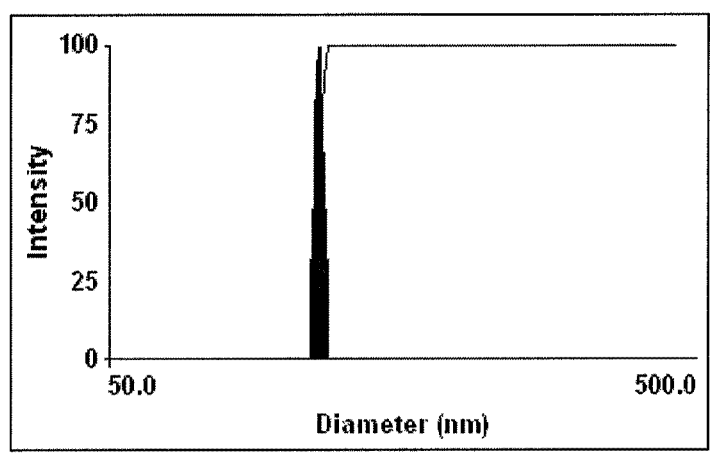
FIG. 12 illustrates the particle size distribution of paclitaxel-loaded GA-PEG-PLGA nanoparticles prepared in Example 10.

Doxorubicin-loaded nanoparticles were prepared by the solvent dialysis method. To DMF (13 mL) were added doxorubicin (15 mg), GA-PEG$_{6000}$-PLGA (50 mg) prepared in the present application and triethylamine (catalytic amount). The mixture was transferred to dialysis bag and dialyzed extensively against distilled water to remove unencapsulated doxorubicin and the organic solvent. The resulting doxorubicin-loading nanoparticle suspension was filtered through a 0.45-μm membrane and then stored at 4° C. Laser light scattering (90-PLUS analyzer, Brookhaven) was used to analysis the particle size distribution of the nanoparticles. The results were shown in FIG. 12. The mean particle size was about 157 nm.

In Vitro Cell Uptake of Nanoparticles

Preparation of FITC-labeled block copolymer

Fluorescein isothiocyanate (FITC) was used as a model fluorescent probe and to modify PLGA-PEG-NH$_2$ to obtain FITC-PEG-PLGA block copolymer.

Preparation of FITC-Labeled Nanoparticles (1) Preparation of FITC-Labeled Nanoparticles Modified with Glycyrrhetinic Acid To acetone (1 mL) were added FITC-PEG-PLGA (5 mg) and GA-PEG-PLGA (25 mg) prepared in the present application at room temperature. The mixture was dropwise added into water (20 mL) with stirring. The remaining acetone was removed to give FITC-labeled nanoparticles.

(2) Preparation of FITC-labeled Nanoparticles without Modification

The process of unmodified nanoparticles is identical to that of the modified nanoparticles, except that mPEG-PLGA was used instead of GA-PEG-PLGA.

In Vitro Cell Uptake of Nanoparticles

Figure 13:
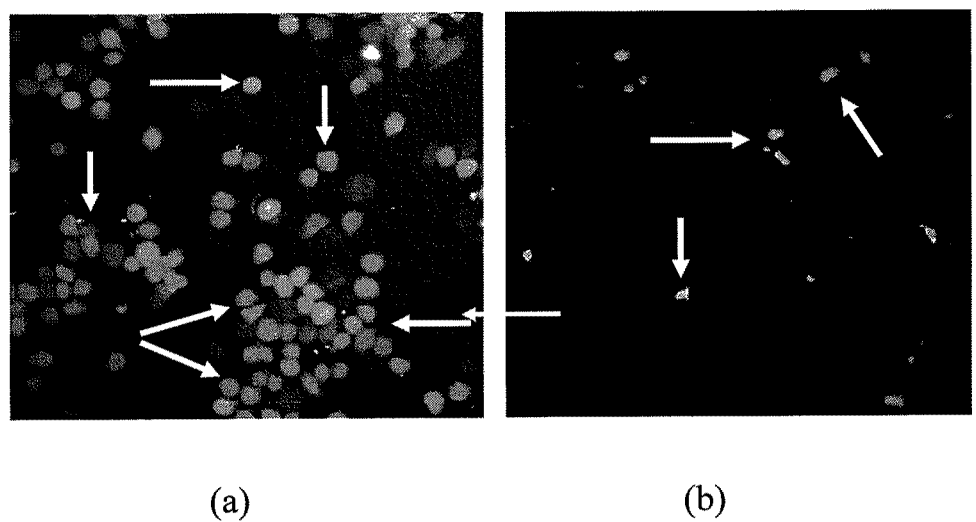
FIG. 13 illustrates the fluorescence images of 7703 hepatic carcinoma cells treated with (a) glycyrrhetinic acid-modified nanoparticles and (b) blank nanoparticles in Example 10.

Human hepatic carcinoma cells 7703 were seeded onto 48-well plates and maintained in 1640 media supplemented with 5% heat-inactivated fetal bovine serum at 37° C. 200 μL of labeled nanoparticles suspension was added to the above plates. After incubation for two hours, the fluorescence images were obtained by fluorescence microscopy (Olympus, Tokyo. Japan). The results were shown in FIG. 13, in which very strong fluorescence was observed in 7703 cells after incubating with glycyrrhetinic acid modified nanoparticles, while weak fluorescence was observed after incubating with those without modification. These results indicated that the nanoparticles bearing glycyrrhetinic acid residues had a high affinity to 7703 cells.

Discussion

Naturally occurring polysaccharides, such as chitosan or derivatives thereof and an alginate, have been received wide attention in the fields of biotechnology and pharmaceuticals for their excellent biocompatibility, biodegradability and nontoxicity. In the present application, the process for preparing nanoparticles of hepatic targeted drug delivery system based on naturally occurring polysaccharides is very novel and simple. The process could be carried out by simple physical mixing and avoid using an organic solvent.

Glycyrrhetinic acid (GA) was modified by diaminopolyethylene glycol to obtain GA-PEG without changing its targeting ability, while greatly enhancing its solubility, and it could easily entangle with naturally occurring polysaccharides. After adding an ion cross-linker, the mixture of GA-PEG and naturally occurring polysaccharides could form a spherical structure and the GA-PEG molecules could either exist in or locate on the surface of the sphere. The in vitro cell tests showed that the nanoparticles modified with glycyrrhetinic acid exhibited a strong affinity with liver cells than those without modification.

Due to the considerable thermodynamic and kinetic stability, polymer micelles formed by synthetic polymers such as PEG-b-poly(amino acid) ester has gained considerable attention. Poly(amino acid) esters act as a hydrophobic segment because they can undergo hydrolytic and enzyme-catalyzed degradations and can be easily excreted from body. While the hydrophilic PEG can effectively prolong the circulation of nanoparticles in blood stream, adsorption by protein shall be prevented and uptake by reticuloendothelial system (RES) shall be lower. Moreover, when the PEG segment modified with targeting ligand in its chain end, it could achieve specific tissue targeting. After introducing diaminopolyethylene glycol to the carriers, the new system is more stable than that disclosed in Chinese patent application No. 200510015172.7 and can be stored up to more than two months without any aggregation or precipitation. In addition, after intravenous injection into the tail veins of rats, about 68% of the total nanoparticles modified with glycyrrhetinic acid accumulates in the livers of rats, which was far more than the unmodified ones. When loaded with anticancer drugs, the system exhibits a continuous release profile for 26 days with a cumulative release amount of about 80.93%.

Polyesters are the most widely used biomaterials for their reasonably good biocompatibility and controllable biodegradability. More importantly, polylactides (PLA), polyglycolides (PGA) and a copolymer of lactide and glycolide (PLGA) have been approved by the U.S. Food and Drug Administration (FDA) and can be commercially available from various sources. In the present application, the hepatic targeted drug carriers were prepared by the condensation reaction between glycyrrhetinic acid and polyesters with diamine (such as ethylenediamine, 1,3-propanediamine, hexanediamine and the like) as space arms. The process is simple and can be easily reproduced. Furthermore, in vitro cell uptake tests show a strong interaction with liver cell via ligand-receptor recognition.

The hepatic targeted drug delivery system of the present application can be easily prepared under mild conditions and can be administered intravenously. Moreover, the hepatic targeted drug delivery system of the present application can greatly enhance the efficacy and selectivity of anticancer drugs and may have a higher prospect for the treatment of liver cancer.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A hepatic targeted nanoparticle comprising an anticancer agent and a carrier comprising a polysaccharide and polyethylene glycol (PEG)-glycyrrhetinic acid (GA)
   wherein the nanoparticle is prepared by a process comprising (a) modifying diamino-PEG with glycyrrhetinic acid (GA) to obtain a GA-modified PEG (PEG-GA);
   (b) physically mixing the PEG-GA with the polysaccharide to obtain a polysaccharide/PEG-GA; and
   (c) loading an anticancer agent to the polysaccharide/PEG-GA with an ion cross-linker to obtain the nanoparticle.

2. A nanoparticle of claim 1, wherein the particle size of the nanoparticle is in the range of about 50 to 450 nm.

3. A nanoparticle of claim 1, wherein the weight of the glycyrrhetinic acid is in the range of about 1-30% by weight of the carrier.

4. A nanoparticle of claim 1, wherein the carrier is biodegradable.

5. A nanoparticle of claim 1, wherein the polyethylene glycol has a molecular weight of about 2,000 to 20,000 Da.

6. A nanoparticle of claim 1, wherein the polysaccharide is chitosan or a derivative thereof and the chitosan or a derivative thereof has a molecular weight of about 3,000 to 200,000Da.

7. A nanoparticle of claim 6, wherein the chitosan derivative is selected from the group consisting of glycol chitosan, O-carboxymethyl chitosan, O-carboxyethyl chitosan, O-carboxypropyl chitosan, O-carboxybutyl chitosan, N, O-carboxymethyl chitosan, N-carboxymethyl chitosan, N,O-sulfur chitosan, 1-deoxygalactit-1-yl -chitosan, 1-deoxygalucit-1-yl-chitosan and N,O-ethylamine chitosan, hydroxymethyl chitosan, hydroxyethyl chitosan, hydroxypropyl chitosan, hydroxyisopropyl chitosan, hydroxybutyl chitosan and N-(2-hydroxyl) -propyl-3-trimethyl ammonium chitosan chloride (HTACC).

8. A nanoparticle of claim 1, wherein the anticancer agent is selected from the group consisting of cisplatin, daunorubicin, doxorubicin hydrochloride, methotrexate sodium, and thioguanine.

9. A pharmaceutical composition comprising the nanoparticle of a hepatic targeted drug delivery system of claim 1 and a pharmaceutically acceptable excipient.

10. A nanoparticle of claim 1, wherein the diamino-PEG is modified with glycyrrhetinic acid (GA) in the presence of dicyclohexyl carbodiimide.

11. A method for inhibiting, relieving, or causing regression of liver cancer in a mammal in need thereof comprising administering a therapeutically effective amount of the nanoparticles of claim 1 to said mammal.

12. A process for preparing a hepatic-targeted nanoparticle comprising an anticancer agent and a carrier comprising polyethylene glycol (PEG)-glycyrrhetinic acid (GA) and a polysaccharide the process comprising
   (a) modifying diamino-PEG with glycyrrhetinic acid (GA) to obtain a GA-modified PEG (PEG-GA);
   (b) physically mixing the PEG-GA with the polysaccharide to obtain a polysaccharide/PEG-GA; and
   (c) loading an anticancer agent to the polysaccharide/PEG-GA with an ion cross-linker to obtain the nanoparticle.

13. A process of claim 12, wherein the carrier is biodegradable.

14. A process of claim 12, wherein the molar ratio of the glycyrrhetinic acid (GA) to the polyethylene glycol (PEG) is in the range of about 0.1 to 5; the mass ratio of the polysaccharide to the glycyrrhetinic acid-poly(ethylene glycol) is in the range of about 0.1 to 10; and the mass ratio of the polysaccharide to the anticancer agent is in the range of about 0.1 to 2.

15. A process of claim 12, wherein the anticancer agent is selected from the group consisting of cisplatin, daunorubicin, doxorubicin hydrochloride, methotrexate sodium, and thioguanine.

16. A process of claim 12, wherein the ion cross-linker is selected from the group consisting of sodium tripolyphosphate, sodium citrate, dextran sulfate and sodium poly(malic acid).

17. A process of claim 12, wherein the process is carried out by physical mixing and no organic solvent is used in the process of preparing the hepatic targeted drug delivery system.

18. A process of claim 12, wherein the diamino-PEG is modified with glycyrrhetinic acid (GA) in the presence of dicyclohexyl carbodiimide.

* * * * *